(12) United States Patent
Suzuki et al.

(10) Patent No.: US 6,683,682 B1
(45) Date of Patent: Jan. 27, 2004

(54) ELECTRONIC COMPONENT INSPECTION EQUIPMENT

(75) Inventors: Yasuyoshi Suzuki, Fujisawa (JP); Masashi Higashi, Matsudo (JP); Akihiko Souda, Hiratsuka (JP)

(73) Assignee: Cognex Technology and Investment Corporation, Mountain View, CA (US)

(*) Notice: Subject to any disclaimer, the term of this patent is extended or adjusted under 35 U.S.C. 154(b) by 0 days.

(21) Appl. No.: 09/527,448

(22) Filed: Mar. 17, 2000

(30) Foreign Application Priority Data

Mar. 19, 1999 (JP) .......................................... 11-075767

(51) Int. Cl.$^7$ ............................................. G01N 21/88
(52) U.S. Cl. ................................ 356/237.1; 356/237.2; 348/126
(58) Field of Search ......................... 356/237.1, 237.2; 348/125, 126, 131

(56) References Cited

U.S. PATENT DOCUMENTS

| | | | |
|---|---|---|---|
| 5,844,249 A | * 12/1998 | Takano et al. | 250/225 |
| 6,005,965 A | * 12/1999 | Tsuda et al. | 250/559.08 |
| 6,191,849 B1 | * 2/2001 | Maeshima et al. | 356/237.1 |

* cited by examiner

*Primary Examiner*—Zandra V. Smith

(57) ABSTRACT

An electronic component inspection equipment effective to prevent reflection of a virtual image in which among side walls of a vessel for accommodating an electronic component, an image pick-up direction to a first side wall is set in a direction of Brewster angle $\Psi_{B1}$ of the first side wall, a first prism and a first polarized light beam splitter are disposed on the image pick-up direction, an image pick-up direction of a second side wall is set in a direction of Brewster angle $\Psi_{B2}$ of the second side wall, and a second prism and a second polarized light beam splitter are disposed on the image pick-up direction.

1 Claim, 8 Drawing Sheets

ELECTRONIC COMPONENT INSPECTION EQUIPMENT

BACKGROUND OF THE INVENTION

1. Field of the Invention

The present invention relates to an electronic component inspection equipment, and more particularly to an electronic component inspection equipment effective to prevent reflection of a virtual image.

2. Description of the Related Art

An electronic component such as a semiconductor device may be shipped in a state wrapped in an embossed tape or the like. Generally, the visual inspection of the electronic component is often conducted immediately before the wrapping. In practice, leads are inspected for their height and pitch deviation when the electronic component is accommodated in the embossed tape. An optical technique using a CCD camera or the like is preferable for the visual inspection of such electronic component.

When an electronic component housed in the embossed tape is optically pictured, however, virtual images of leads reflected in the side walls of the embossed tape might also be pictured other than the electronic component body. The virtual images of leads reflected in the side walls of the embossed tape make it difficult to judge an actual portion, possibly hindering the inspection.

Japanese Patent Application Laid-Open Publication No. 10-148517 has proposed an image pick-up technique in that the Brewster angle is used as means effective for preventing Ha phenomenon that the virtual image is reflected. This technique is based on the point that the reflection of a P polarized light wave becomes minimum at the Brewster angle and determines an image pick-up direction of a camera to be fat the Brewster angle to the walls of the embossed tape so to pick up an image of leads of the electronic component by irradiating a P polarized light wave from the determined position.

But, it was found that the above technique has a disadvantage that when it is used to inspect the leads of an electronic component, the leads are somewhat reflected, and its resolution is required. This problem is particularly conspicuous with QFP (Quad Flat Package).

SUMMARY OF THE INVENTION

Under the circumstances described above, it is an object of the present invention to provide an electronic component inspection equipment effective to prevent reflection of a virtual image.

To achieve the above object, a first aspect of the invention is an electronic component inspection equipment for optically inspecting an external shape of an electronic component (12) accommodated in a vessel (10), comprising: illumination means (M10) for irradiating illumination light (14) to the electronic component; image pick-up means (M12) which determines a direction satisfying a Brewster angle to a side wall (16) of the vessel as an image pick-up direction (18); and polarized light wave selection means (M14) which is disposed on the image pick-up direction to preferentially select a P polarized light wave to the side wall and leads the selected P polarized light wave to the image pick-up means.

A second aspect of the invention is in accordance with the first aspect of the invention in which the polarized light wave selection means (M14) is formed of a polarizer, and the image pick-up means is disposed on an optical path of the P polarized light wave selected by the polarizer.

A third aspect of the invention is in accordance with the second aspect of the invention in which the polarizer is a polarized light beam splitter.

A fourth aspect of the invention is in accordance with the second aspect of the invention in which the polarizer is a polarizing filter.

A fifth aspect of the invention is an electronic component inspection equipment for optically inspecting an external shape of an electronic component accommodated in a vessel (10), comprising: illumination means (M10) for irradiating illumination light (14) to the electronic component; image pick-up means (M12) which determines as image pick-up directions both a first direction (18-1) satisfying a Brewster angle to a first side wall (16-1) of the vessel and a second direction (18^2) satisfying the Brewster angle toga second side wall (16-2) having an angle with respect to the first side wall; first selection means (M14-1) which is disposed on the first direction to preferentially select P polarized light wave to the first side wall and leads the selected P polarized light wave to the image pick-up means; and second selection means (M14-2) which is disposed on the second direction to preferentially select P polarized light wave to the second side wall and leads the selected P polarized light wave to the image pick-up means.

A sixth aspect of the invention is in accordance with the fifth aspect of the invention in which the first selection means and the second selection means are respectively formed of a polarizer, the image pick-up means is disposed on optical paths of the P polarized light wave to the first side wall and the P polarized light wave to the second side wall respectively selected by the individual polarizers.

A seventh aspect of the invention is in accordance with the fifth aspect of the invention in which the first selection means and the second selection means are formed of a single polarizer, ½λ plate (32) which turns the oscillation direction of the P polarized light wave to the second side wall by 90 degrees is disposed between the polarizer and the second side wall, and the image pick-up means is disposed on an optical path of the P polarized light wave with respect to the first side wall selected by the polarizer.

An eighth aspect of the invention is in accordance with the sixth or seventh aspect of the invention in which the polarizer is a polarized light beam splitter.

A ninth aspect of the invention is in accordance with the sixth or seventh aspect of the invention in which the polarizer is a polarizing filter.

DESCRIPTION OF THE PREFERRED EMBODIMENTS

Figure 1:
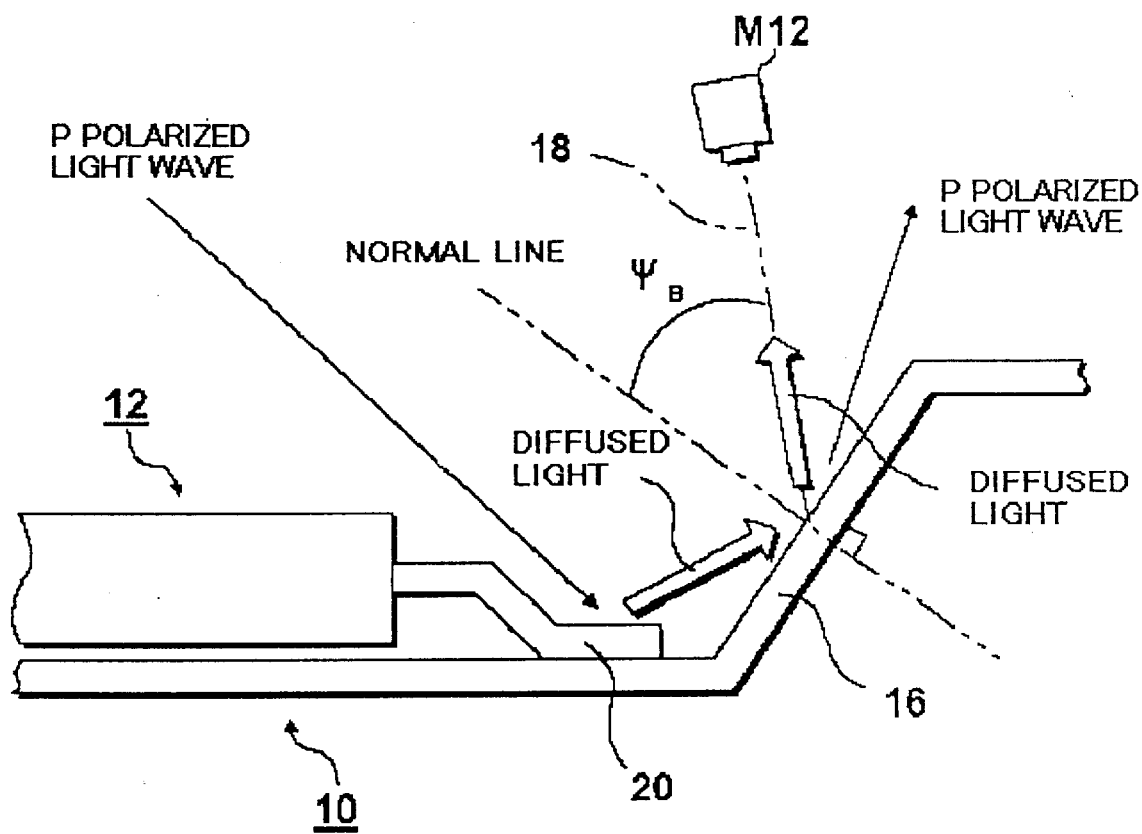
FIG. 1 is a schematic side view showing a phenomenon that diffused light is generated when an electronic component is inspected for its shape.

The invention has a major feature that a P polarized light component of a virtual image is evaded by the Brewster angle and elements other than the P polarized light component are positively attenuated. Thus, an influence of the polarized light component which was not able to be removed completely by the Brewster angle only is decreased and reflection of the virtual image can be prevented.

The inventor thought first that the reflection of the virtual image was caused regardless of the use of the Brewster angle as follows. The following descriptions will be made mainly in connection with the process of the invention, and details of the respective elements shown in the drawings will be described afterward.

FIG. 1 is a schematic side view showing a phenomenon that diffused light is generated when an electronic component is inspected for its shape. As shown in FIG. 1, the technology of Japanese Patent Application Laid-Open Publication No. 10-148517 describes that electronic component 12 is pictured with image pick-up direction 18 of image pick-up means M12 set to Brewster angle ΨB with respect to side wall surface 16 and P polarized light wave used as lighting. The P polarized light wave used for lighting is considered to be in the following operating condition.

The P polarized light wave irradiated to lead 20 of the electronic component 12 travels as it is to reach the lead 20. Then, the P polarized light wave is reflected by the lead 20 and diffused its oscillation directions to become diffused light. The reason for this is considered that the surface of the lead 20 is a diffusing surface. The diffused light generated on the lead 20 is reflected by the side wall 16 of vessel 10 so to be further diffused. As shown in FIG. 1, P polarized light component in the diffused light travels off the Brewster angled ΨB, while polarized light components other than the P polarized light component travels in the image pick-up direction 18 set to the Brewster angle of the side wall 16. As a result, the polarized light components other than the P polarized light component are entered the image pick-up means M12, and its virtual image is pictured.

The inventor also thought about the cause that reflection of the virtual image becomes conspicuous at the inspection of QFP as follows.

Figure 2:
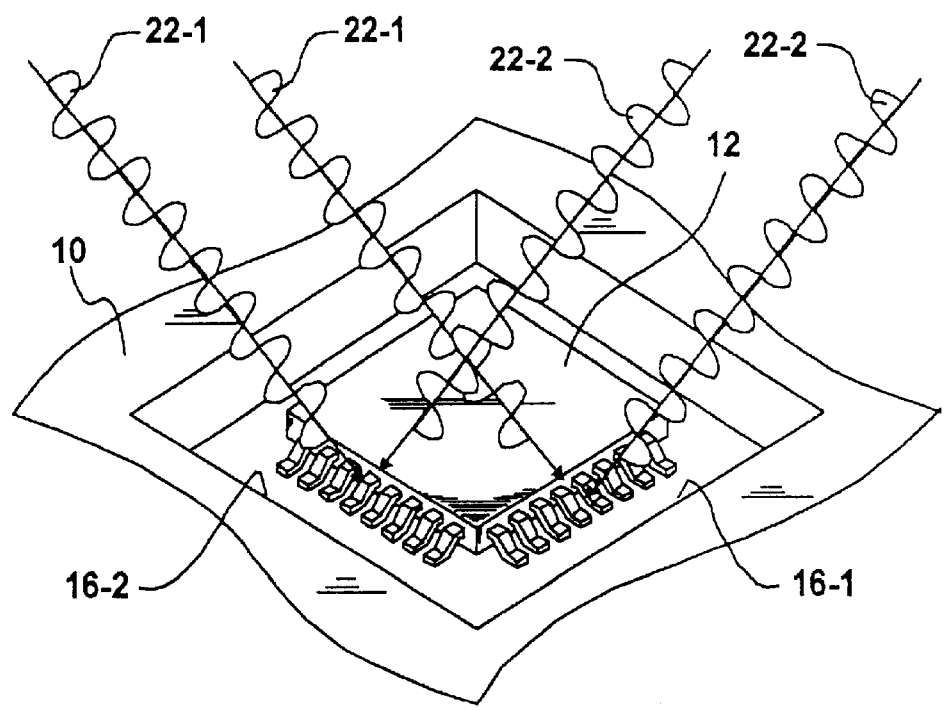
FIG. 2 is a schematic perspective view showing oscillation directions of two kinds of polarized light waves entered different sides when QFP is inspected for its shape.

FIG. 2 is a schematic perspective view showing oscillation directions of two types of polarized light waves which are entered different sides in the shape inspection of QFP. There is a problem of the reflection in all the side walls of the vessel 10 because the electronic component 12 of the QFP type has the leads on its four sides respectively as shown in FIG. 2. Here, the side walls of the vessel 10 can be classified into two groups, namely first side wall 16-1 and second side wall 16-2, with reference to the direction of each side wall. In order prevent the reflection in the first side wall 16-1 and the second side wall 16-2, it is necessary to irradiate first polarized light wave 22-1 and second polarized light wave 22-2, which become P polarized light to each side wall, as illumination light to the first side wall 16-1 and the second side wall 16-2. The first polarized light wave 22-1 and the second polarized light wave 22-2 which become the P polarized light with respect to the individual side walls have a different waveform because there is an angle of about 90 degrees between the first side wall-16-1 and the second side wall 16-2. Therefore, two types of polarized light waves are irradiated to the respective leads of QFP.

Figure 3:
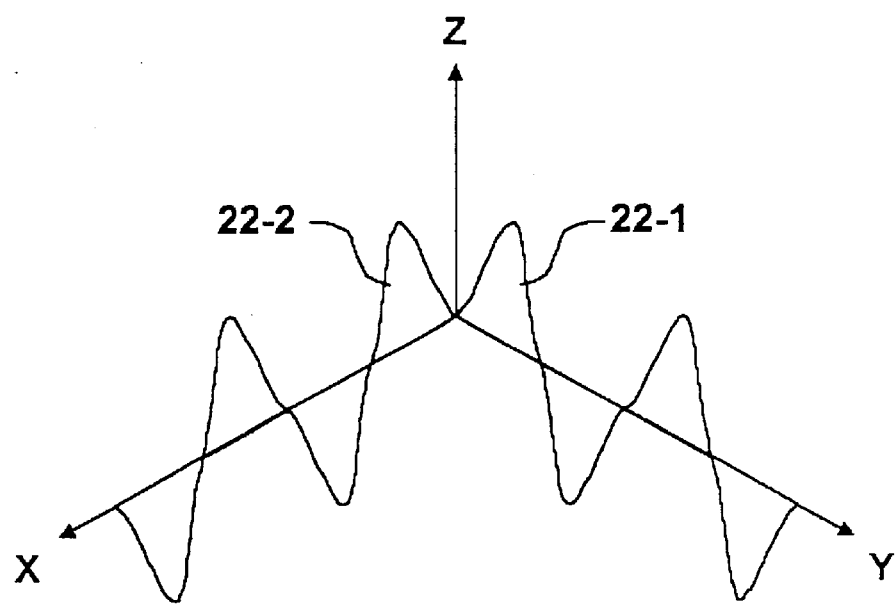
FIG. 3 is a schematic perspective view showing waveforms of first and second polarized light waves 22-1, 22-2 shown in FIG. 2.

FIG. 3 is a schematic perspective view showing waveforms of the first polarized light wave 22-1 and the second polarized light wave 22-2-shown in FIG. 2. As shown in FIG. 3, the first polarized light wave 22-1 irradiated to the first side wall 16-1 oscillates on a Z-Y plane, and the second polarized light wave 22-2 irradiated to the second side wall 16-2 oscillates on a Z-X plane. Thus, when both the first polarized light wave 22-1 and the second polarized light wave 22-2 which have a different oscillating plane are emitted as shown in FIG. 2, it is assumed that diffused light is produced by admixing of the two different polarized light waves. Thus, the diffused light produced as described above enters the image pick-up means M12 in the same way as the case of FIG. 1.

Considering as described above, the inventor has judged that the image pickup by the P polarized light only is physically difficult and conducted research to eliminate the diffused light which travels in the image pick-up direction 18. But, complete interception of the incident light to the image pick-up means M12 disables the image pickup of the actual portion. Based on the above viewpoint, research activity was repeatedly conducted to achieve the present invention that provides a structure effective to prevent reflection of a virtual image. Now, this characteristic novel structure will be described in detail.

First Aspect

Figure 4:
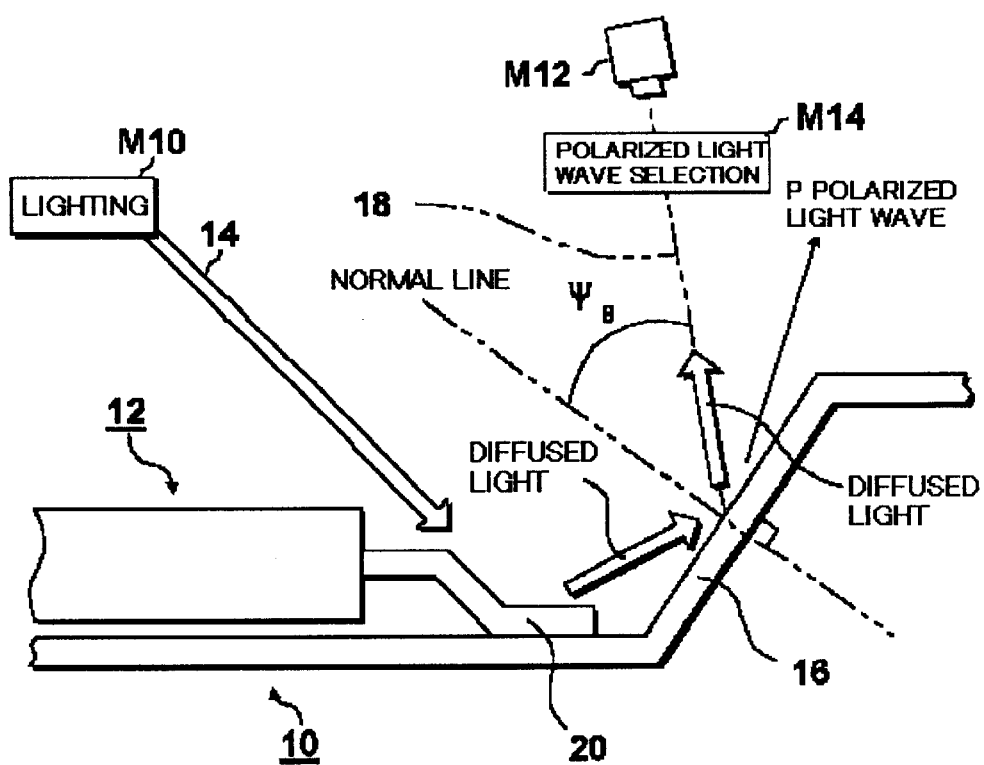
FIG. 4 is a schematic side view showing a structure of the electronic component inspection equipment according to a first aspect of the invention.

FIG. 4 is a schematic side view showing a structure of the electronic component inspection equipment according to a first aspect of the present invention. The structure of the first aspect of the invention will be described with reference to FIG. 4.

The electronic component 12 is a component to be inspected according to the invention and includes a semiconductor device, a chip coil, a chip resistor and other surface-mounted parts. This electronic component 12 has lead 20 which serves as an external electrode terminal when the electronic component 12 is mounted. And it is a major object of the invention to accurately inspect a shape of the lead 20.

Vessel 10 has an accommodation space surrounded by side walls 16 to accommodate the electronic component 12 therein. An embossed tape is one aspect of this vessel 10. Generally, the side walls 16 of the vessel 10 are formed not to be perpendicular but somewhat diagonally to facilitate the removal of the electronic component. A possibility of reflection of the virtual image is variable depending on an angle of inclination of the side walls 16, but the present invention can be applied to any angle of inclination.

Lighting means M10 is disposed above the vessel 10 to irradiate illumination light 14 to the electronic component 12. The illumination light 14 may be any of P polarized light, diffused light, and linear polarized light. As shown in FIG. 4, the illumination light 14 irradiated to the lead 20 is reflected by the lead 20 and becomes diffused light. Thus, the illumination light 14 contains diffusion components to some extent after its reflection by the lead 20 regardless of whatever polarized light wave is entered. Therefore, the diffused light can be used satisfactory for the illumination light 14 from the beginning.

The image pick-up means M12 is set toward a direction to satisfy the Brewster angle with respect to the sidewall side 16 of the vessel 10 as image pick-up direction 18 to take picture of the electronic component 12 in this direction. The direction to satisfy the Brewster angle means a direction inclined from the normal line to the sidewall side 16 by only Brewster angle $\Psi B$. The reason to determine the direction satisfying the Brewster angle as the image pick-up direction 18 is to avoid P polarized light component of a virtual image which reflects in the sidewall side 16. What is propagating toward the image pick-up direction 18 among the virtual images reflected by the sidewall 16 becomes elements other than the P polarized light. The optical image pick-up devices such as CCD cameras are included in this image pick-up means M12.

Polarized light wave selection means M14 is disposed above the image pick-up direction 18 to select the P polarized light wave to the sidewall 16 with priority so to guide the selected P polarized light wave to the image pick-up means M12. The P polarized light wave to the side wall 16 is a polarized light wave which oscillates in parallel to a plane including an incident light path of the polarized light wave and the normal line to the side wall 16. The polarized light component intentionally removed from the image pick-up direction 18 by the effect of the Brewster angle is the P polarized light wave to the side wall 16.

The "selection of the P polarized light wave to the side wall 16" means removal of elements other than the P polarized light from the image pick-up direction 18. Thus, the P polarized light wave is lead to the image pick-up means M12 with priority. A method of selecting the P polarized light wave may intercept or attenuate the elements other than the P polarized light wave with a polarizing filter. By arranging the polarizing filter in the step before the image pick-up means M12, the elements other than the P polarized light are attenuated by the polarizing filter to select the P polarized light wave with the higher priority. The interception or attenuation by this polarizing filter is not limited to the attenuation of all elements other than the P polarized light but also includes the interception and attenuation of even one element other than the P polarized light. Therefore, the concept of this interception and attenuation can be considered from the opposite point of view to be indicated as a concept of selectively penetrating the P polarized light wave. The element which should be especially considered as an attenuation target among the elements other than the P polarized light is S polarized light component. The reason for this is that the S polarized light wave remains on the image pick-up direction 18 when the P polarized light wave is removed at the Brewster angle among the diffused light reflected by the side wall 16. Therefore, substantial attenuation of S polarized light component is the "selection of the P polarized light wave with the higher priority". Thus, the P polarized light component of the virtual image reflected in the side wall 16 is removed at the Brewster angle, and the S polarized light component is removed by the polarized light wave selection means M14. On the other hand, at least the P polarized light component among the real images of the electronic component 12 penetrates the polarized light wave selection means 14, so that the teal image portion is entered the image pick-up means M12 without fail. As a result, it becomes possible to conduct the image pickup with only the virtual image portion selectively attenuated.

Polarizer such as a beam splitter can also be used as means for selecting the P polarized light wave. The optical paths of the P polarized light wave and the elements other than the P polarized light wave are separated before the image pick-up means M12 by the polarizer disposed in the step before the image pick-up means M12. The P polarized light wave can be selected with priority by setting the optical path of this separated P polarized light wave along the image pick-up direction 18. Such a state can be produced by a positional relation between the image pick-up means M12 and the polarizer. The method of using the polarizer can be expressed by a concept that a specific polarized light component is reflected to lead the P polarized light wave to the image pick-up means M12.

According to the first aspect of the invention described above, the reflection of the virtual image can be prevented effectively because the P polarized light component among the virtual images reflected by the side wall 16 gets out of the image pick-up direction 18 set to the Brewster angle and other polarized light components are removed before the image pick-up means M12.

Second Aspect

A second aspect of the invention exemplifies a possibility of applying the present invention to QFP.

Figure 5:
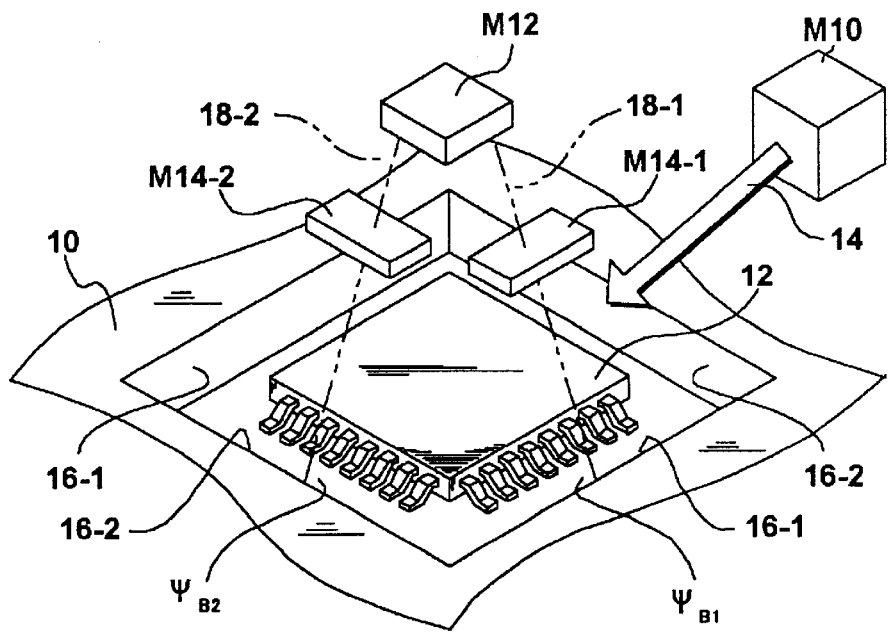
FIG. 5 is a schematic perspective view showing a structure of the electronic component inspection equipment according to a second aspect of the invention.

FIG. 5 is a schematic perspective view showing a structure of the electronic component inspection equipment according to the second aspect of the invention. The second aspect of the invention will be described with reference to FIG. 5. Like reference numerals will be used to designate like elements as in the first aspect above and their descriptions will be omitted. And, portions different from the first aspect will be mainly described below.

First side wall 16-1 and second side wall 16-2 are based on a concept that the side walls surrounding the electronic component 12 are classified into two groups in view of directions of their planes. As shown in FIG. 5, the first side wall 16-1 and the second side wall 16-2 are mutually disposed at a predetermined angle to form a space for accommodating the electronic component 12. The electronic component 12 of the QFP type has leads on its four sides, so that the virtual images of the leads are reflected in the respective side walls.

First direction 18-1 and second direction 18-2 satisfy Brewster angles $\Psi B1$, $\Psi B2$ with respect to the first side wall 16-1 and the second side wall 16-2. The first direction 18-1 and the second direction 18-2 are set along an image pick-up direction of the image pick-up means M12. Thus, among the virtual images reflected in the first side wall 16-1, the P polarized light component to the first side wall 16-1 progresses off the first direction 18-1. And, among the virtual images reflected in the second side wall 16-2, the P polarized light component to the second side wall 16-2 progresses off the second direction 18-2.

The first selection means M14-1 and the second selection means M14-2 are disposed on the first direction 18-1 and the second direction 18-2 respectively and select with priority the P polarized light wave to the first side wall 16-1 and the second side wall 16-2 respectively to lead the selected P polarized light wave to the image pick-up means M12. Thus, among the virtual images reflected in the first side wall 16-1 and the second side wall 16-2, the P polarized light component is removed respectively at the Brewster angles ΨB1 and ΨB2, and other components are removed by the first selection means M14-1 and the second selection means M14-2 respectively. The first selection means M14-1 and the second selection means M14-2 can be configured by using the polarizer and the polarizing filter in the same way as the polarized light wave selection means M14 of the first aspect described above. Various variations are considered for the positional relation of the polarizer, the polarizing filter and the image pick-up means. Such examples will be described in the embodiments below.

According to the second aspect of the invention described above, the reflection of the leads of QFP can be prevented effectively because the Brewster angle is set for the two side walls having a different angle respectively and the means for selecting the P polarized light component with priority is disposed.

EMBODIMENTS

Summary

Figure 6:
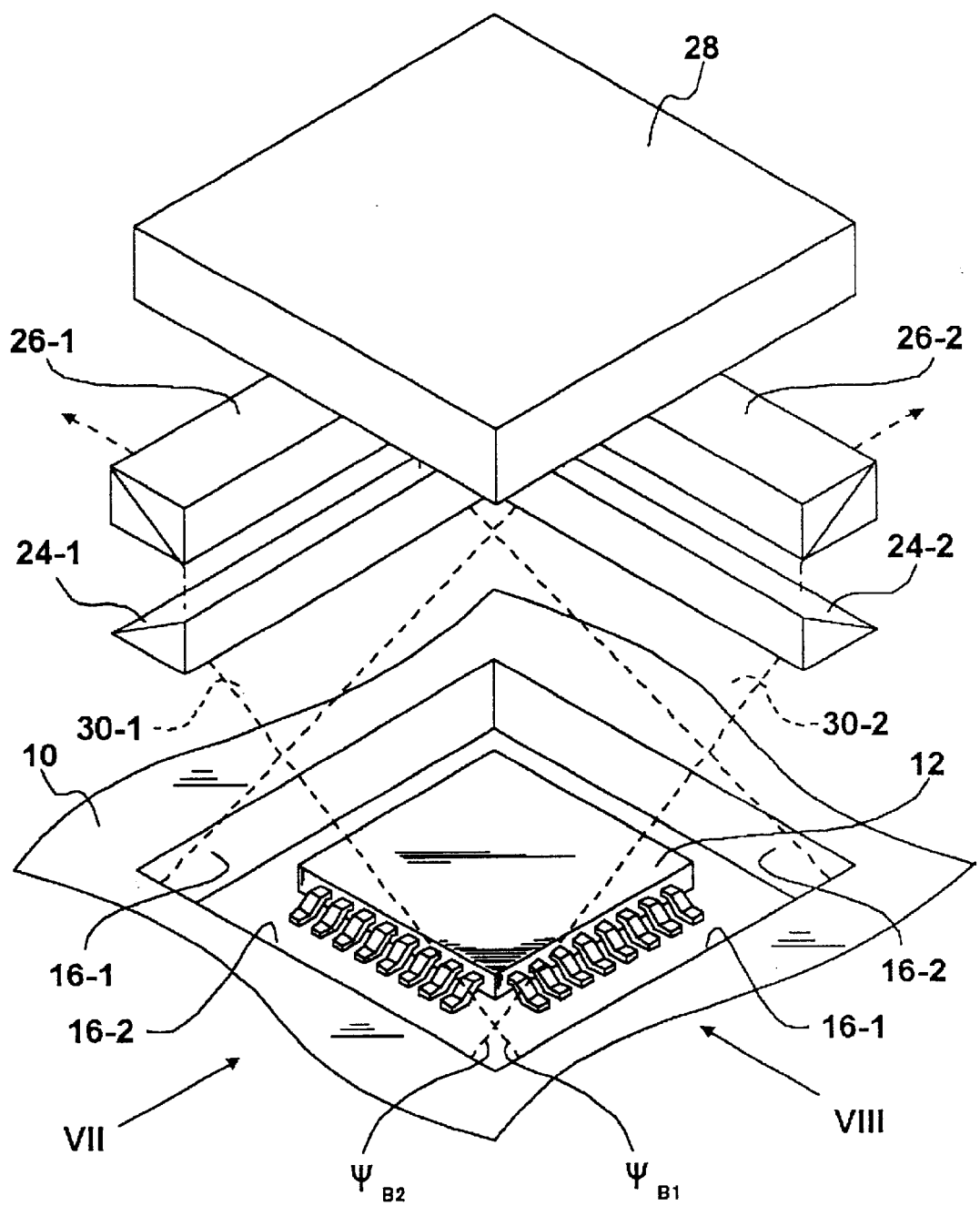
FIG. 6 is a perspective view showing a structure of the electronic component inspection equipment according to a first embodiment of the invention.

Referring to FIG. 6, among the side walls of the vessel 10 for accommodating the electronic component 12, the image pick-up direction of the first side wall 16-1 is determined in a direction of its Brewster angle ΨB1, and first prism 24-1 and first polarized light beam splitter 26-1 are disposed on that image pick-up direction. Similarly, the image pick-up direction of the second side wall 16-2 is determined in a direction of its Brewster angle. ΨB2, and second prism 24-2 and second polarized light beam splitter 26-2 are disposed on that image pick-up direction.

First Embodiment

A lot of P polarized light components and S polarized light components are included in the virtual images reflected in the side walls of the vessel. Therefore, some examples of optical arrangements to remove both the P polarized light components and the S polarized light components will be presented as preferable embodiments of the invention. In the following descriptions, details of the same elements as the elements described above will not be described.

FIG. 6 is a perspective view showing a structure of the electronic component inspection equipment according to a first embodiment of the invention. As shown in FIG. 6, among the virtual images reflected in the first side wall 16-1 and the second side wall 16-2, those propagating in directions of. Brewster angles ΨB1, ΨB2 are S polarized light wave 30-1 to the first side wall and S polarized light wave 30-2 to the second side wall.

Therefore, the first prism 24-1 and the second prism 24-2 are respectively disposed on the optical path of the each S polarized light wave to change the optical path of the each S polarized light wave in a perpendicular direction. Only two prisms are shown in FIG. 6 to specifically show the optical path of the S polarized light wave, but four prisms are actually disposed in correspondence with the four side walls. The first polarized light beam splitter 26-1 and the second polarized light beam splitter 26-2 are disposed directly above the first prism 24-1 and the second prism 24-2 so to horizontally emit the S polarized light wave having passed through the each prism. Specifically, the first polarized light beam splitter 26-1 and the second polarized light beam splitter 26-2 displace the optical paths of the S polarized light wave 30-1 to the first side wall and the S polarized light wave 30-2 to the second side wall from the image pick-up direction of image pick-up camera 28 so to prevent the each S polarized light wave from entering the image pick-up camera 28. In actual practice, the first polarized light beam splitter 26-1 and the second polarized beam splitter 26-2 are also disposed in four in the same way as the first prism 24-1 and the second prism 24-2.

Figure 7:
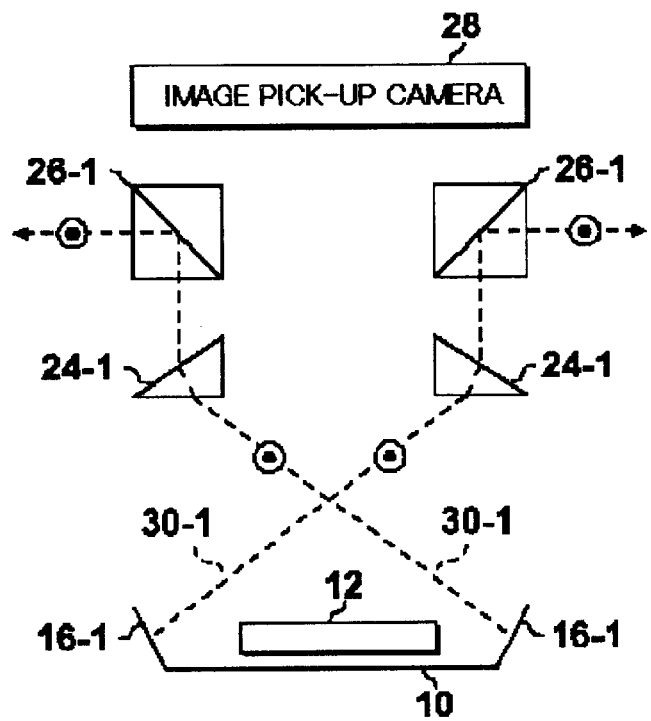
FIG. 7 is a schematic side view showing optical paths and oscillation directions of S polarized light waves 30-1 to first side walls viewed from direction VII of FIG. 6.

FIG. 7 is a schematic side view showing an optical path and an oscillation direction of the S polarized light wave 30-1 to the first side wall viewed from direction VII of FIG. 6. As shown in FIG. 7, the S polarized light wave 30-1 to the first side wall oscillates in a direction parallel to the first side wall 16-1. Specifically, the S polarized light wave 30-1 oscillates back and forth between this side and the other side of the drawing sheet. An arrow is used to indicate a portion where the S polarized light wave 30-1 oscillates in a direction to pass through the drawing sheet. And, the S polarized light wave oscillates in the direction to pass through the drawing sheet to penetrate the first prism 24-1 and then displaced from the image pick-up direction of the image pick-up camera 28 by the first polarized beam splitter 26-1.

Figure 8:
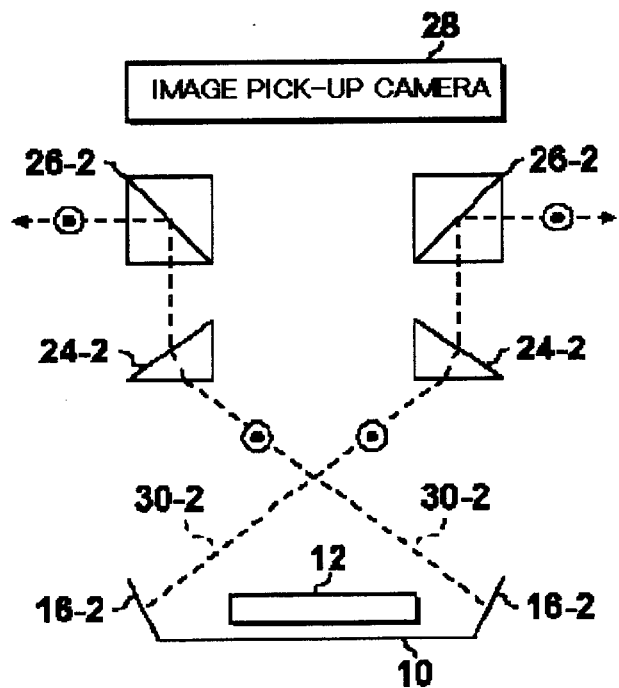
FIG. 8 is schematic side view showing optical paths and oscillation directions of S polarized light waves 30-2 to second side walls viewed from direction VIII of FIG. 6.

FIG. 8 is a schematic side view showing an optical path and an oscillation direction of the S polarized light wave 30-2 to the second side wall viewed from direction VIII of FIG. 6. As shown in FIG. 8, the S polarized light wave 30-2 to the second side wall oscillates in a direction parallel to the second side wall 16-2. In other words, the S polarized light wave 30-2 oscillates back and forth between this side and the other side of the drawing sheet. And, the S polarized light wave oscillates in the direction to pass through the drawing sheet to penetrate the second prism 24-2 and then is displaced from the image pick-up direction of the image pick-up camera 28 by the second polarized light beam splitter 26-2. Thus, the virtual images of the electronic component 12 reflected in the side walls of the vessel 10 are removed.

Second Embodiment

Figure 9:
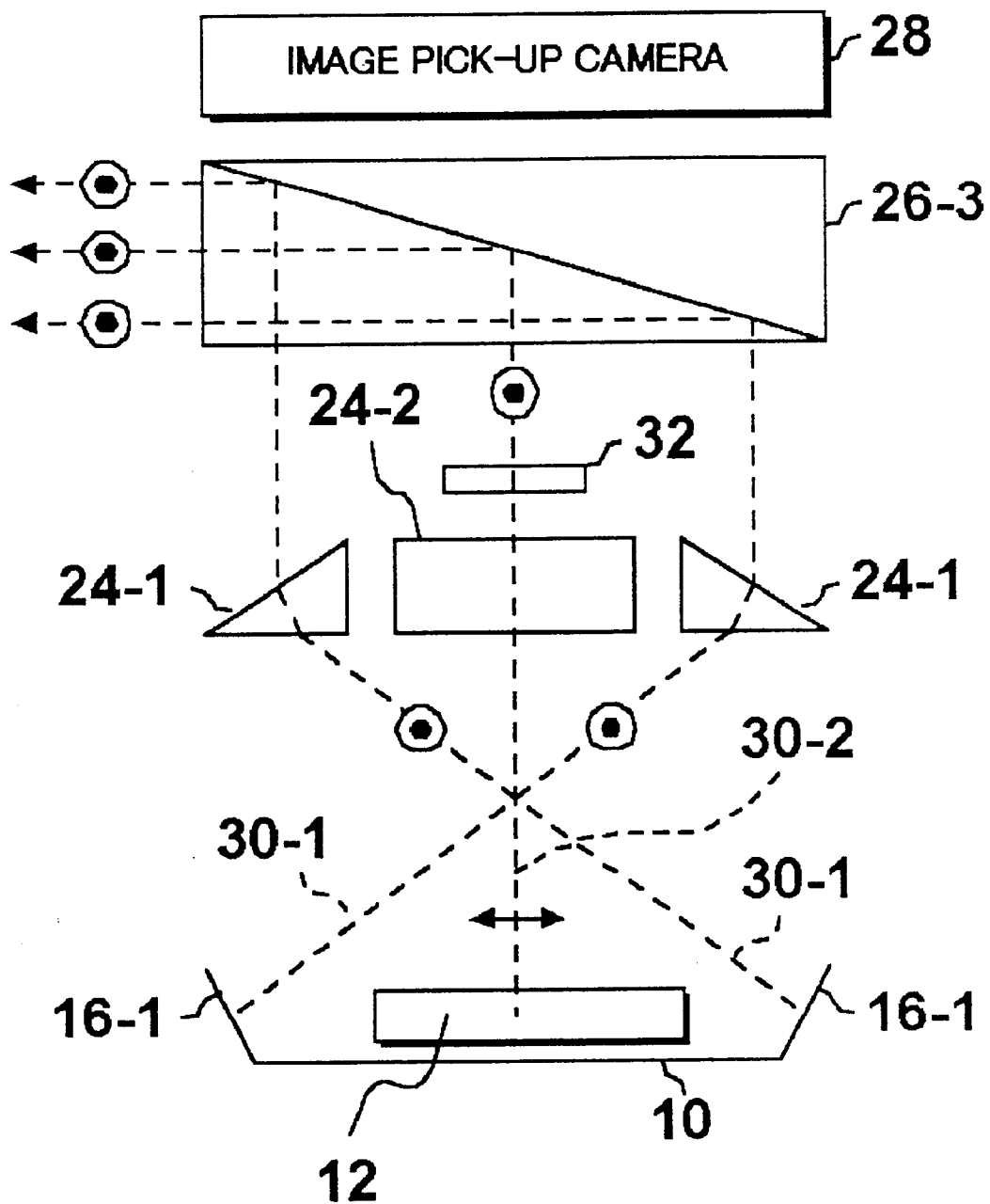
FIG. 9 is a schematic side view showing a structure of the electronic component inspection equipment according to a second embodiment of the invention.

FIG. 9 is a schematic side view showing a structure of the electronic component inspection equipment according to a second embodiment of the invention. FIG. 9 corresponds to FIG. 7 of the first embodiment described above. In this embodiment, a single polarizer is used to remove the S polarized light wave 30-1 to the first side wall and the S polarized light wave 30-2 to the second side wall from the image pick-up regions. Third polarized light beam splitter 26-3 used in this embodiment is an element for removing a polarized light wave oscillating in a direction to pass through the drawing sheet as shown in FIG. 9.

As shown in FIG. 9, when the S polarized light wave is observed from a direction parallel to the first side wall 16-1, the S polarized light wave 30-1 to the first side wall oscillates in a direction to pass through the drawing sheet, and the S polarized light wave 30-2 to the second side wall oscillates on the drawing sheet. Therefore, the S polarized light wave 30-2 to the second side wall cannot be removed by the third polarized light beam splitter 26-3. Therefore, ½λ plate 32 is disposed immediately above the second prism 24-2 and turns the oscillation direction of the S polarized light wave by 90 degrees. As a result, the S polarized light wave having passed through the ½λ plate 32 oscillates in a direction to pass through the drawing sheet and is removed from the image pick-up region by the third polarized beam splitter 26-3.

Third Embodiment

Figure 10:
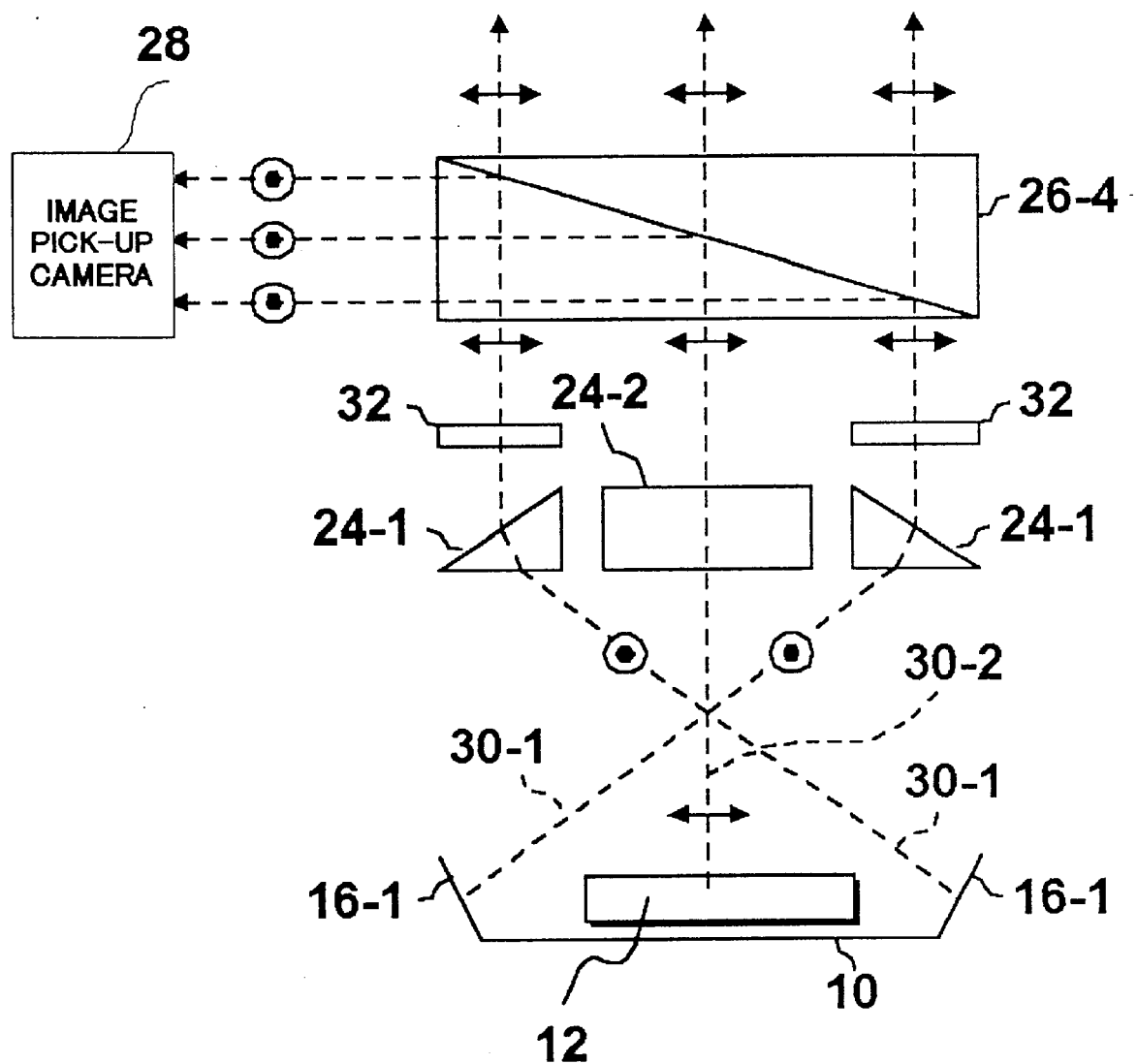
FIG. 10 is a schematic side view showing a structure of the electronic component inspection equipment according to a third embodiment of the invention.

FIG. 10 is a schematic side view showing a structure of the electronic component inspection equipment according to a third embodiment of the invention. FIG. 10 corresponds to FIG. 9 of the second embodiment described above. The third embodiment corresponds to the second embodiment except that a type of the polarizer and a position of the image pick-up camera 28 are changed.

Specifically, fourth polarized light beam splitter 26-4 of this embodiment is used to replace the third polarized light beam splitter 26-3 shown in FIG. 9. The fourth polarized light beam splitter 26-4 is an element for allowing the polarized light wave oscillating on the drawing sheet to pass through it and reflecting the polarized light wave oscillating in a direction perpendicular to the drawing sheet in a perpendicular direction. And, the ½λ plate 32 is disposed not immediately above the second prism 24-2 but the first prism 24-1, and the image pick-up camera 28 is disposed on the side of the fourth polarized light beam splitter. By disposing as described above, the oscillation direction of the S polarized light wave 30-1 is turned by 90 degrees by the ½λ plate 32 to become a polarized light wave oscillating on the drawing sheet. As a result, the component of the virtual image penetrate the polarizer 26-4 and is displaced from the image pick-up camera 28. And, components other than the virtual image oscillating in a direction perpendicular to the drawing sheet is lead to the image pick-up camera 28. Thus, the image pickup is performed without involving the virtual images reflected in the side walls of the vessel.

Fourth Embodiment

Figure 11:
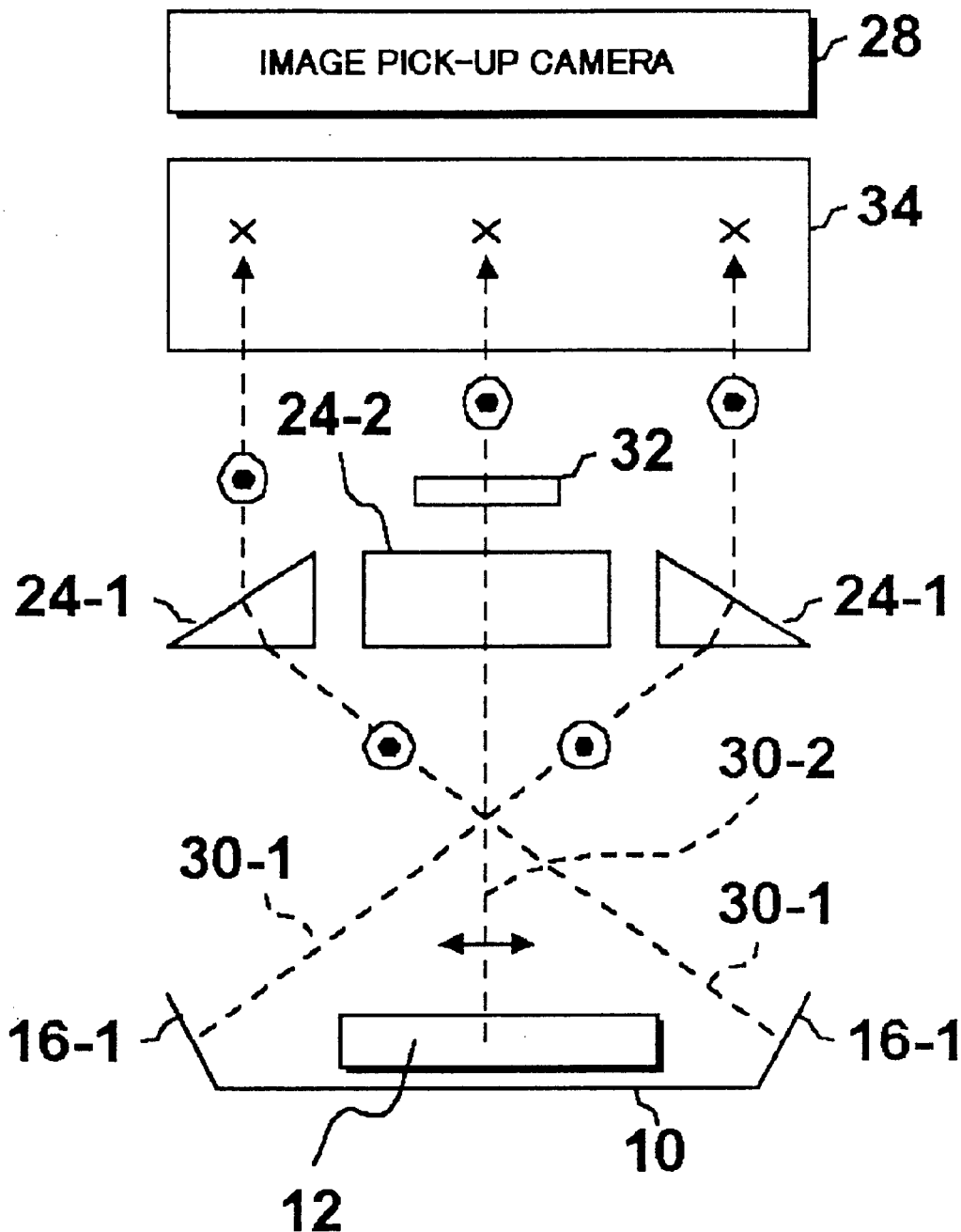
FIG. 11 is a schematic side view showing a structure of the electronic component inspection equipment according to a fourth embodiment of the invention

FIG. 11 is a schematic side view showing a structure of the electronic component inspection equipment according to a fourth embodiment of the invention. FIG. 11 corresponds to FIG. 9 of the first embodiment described above. In the fourth embodiment, polarizing filter 34 is used to intercept the S polarized light wave 30-1 to the first side wall and the S polarized light wave 30-2 to the second side wall and leads the P polarized light components to the image pick-up camera 28. The polarizing filter 34-used in this embodiment is an element for removing the polarized light wave oscillating in a direction to pass through the drawing sheet as shown in FIG. 11. The ½λ plate 23 is disposed immediately above the second prism 24-2 in the same way as in the aforesaid embodiment.

What is claimed is:

1. An electronic component inspection equipment for optically inspecting an external shape of an electronic component accommodated in a vessel, comprising:

illumination means for irradiating illumination light to the electronic component;

image pick-up means which determines as image pick-up directions both a first direction satisfying a Brewster angle to a first side wall of the vessel and a second direction satisfying the Brewster angle to a second side wall having an angle with respect to the first side wall;

first selection means which is disposed on the first direction to preferentially select P polarized light wave to the first side wall and leads the selected P polarized light wave to the image pick-up means; and second selection means which is disposed on the second direction to preferentially select P polarized light wave to the second side wall and leads the selected P polarized light wave to the image pick-up means.

* * * * *